US010888672B1

(12) United States Patent
Vitello

(10) Patent No.: US 10,888,672 B1
(45) Date of Patent: Jan. 12, 2021

(54) TAMPER EVIDENT CLOSURE ASSEMBLY FOR A MEDICAL DEVICE

(71) Applicant: Patrick Vitello, Fort Lauderdale, FL (US)

(72) Inventor: Patrick Vitello, Fort Lauderdale, FL (US)

(73) Assignee: International Medical Industries, Inc., Pompano Beach, FL (US)

( * ) Notice: Subject to any disclaimer, the term of this patent is extended or adjusted under 35 U.S.C. 154(b) by 266 days.

(21) Appl. No.: 15/947,528

(22) Filed: Apr. 6, 2018

Related U.S. Application Data

(60) Provisional application No. 62/482,490, filed on Apr. 6, 2017.

(51) Int. Cl.
*A61M 5/50* (2006.01)
*A61M 39/10* (2006.01)
*A61M 5/32* (2006.01)
*A61M 5/31* (2006.01)

(52) U.S. Cl.
CPC ........ *A61M 5/5086* (2013.01); *A61M 5/3202* (2013.01); *A61M 39/1011* (2013.01); *A61M 2005/3104* (2013.01); *A61M 2005/3118* (2013.01)

(58) Field of Classification Search
CPC .............. A61M 5/5086; A61M 5/3202; A61M 2005/3118; A61M 2005/3104; A61M 39/1011
See application file for complete search history.

(56) References Cited

U.S. PATENT DOCUMENTS

| 732,662 A | 6/1903 | Smith |
| 1,678,991 A | 7/1928 | Marschalek |
| 1,970,631 A | 8/1934 | Sherman |
| 2,477,598 A | 2/1948 | Hain |
| 2,739,590 A | 3/1956 | Yochem |
| 2,823,674 A | 2/1958 | Yochem |

(Continued)

FOREIGN PATENT DOCUMENTS

| EP | 0148116 A | 7/1985 |
| WO | WO 2008/000279 | 1/2008 |
| WO | WO 2017086607 | 5/2015 |

*Primary Examiner* — Laura A Bouchelle
*Assistant Examiner* — Anh Bui
(74) *Attorney, Agent, or Firm* — Malloy and Malloy, PA; Jennie Malloy

(57) ABSTRACT

A closure assembly for a medical device including an administering device such as, but not limited to, a prefilled syringe, includes a housing having an access opening, a stop member disposed therein and an end cap. A tip cap, attachable in a flow restricting relation to the medical device is disposed within the housing and is removably connected to a base, wherein the stop member restricts removal of the flow restrictor from the housing through the access opening. The base is disposed in a captured orientation between the stop member and the end cap. The flow restrictor is disconnected from the base when a predetermined force is applied to flow restrictor, as the housing is rotationally attached to the medical device. The flow restrictor remains attached in flow restricting relation to the medical device while being disconnected from the base until the housing is detached from the medical device.

15 Claims, 2 Drawing Sheets

(56) References Cited

U.S. PATENT DOCUMENTS

| | | |
|---|---|---|
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,368,673 A | 2/1968 | Johnson |
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,747,751 A | 4/1973 | Miller et al. |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A | 6/1987 | Nordgren et al. |
| 4,693,707 A | 9/1987 | Dye |
| 4,726,483 A | 2/1988 | Drozd |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,049,129 A | 9/1991 | Zdeb et al. |
| 5,051,093 A | 10/1991 | Clegg et al. |
| D323,392 S | 1/1992 | Byrne |
| 5,135,496 A | 8/1992 | Vetter et al. |
| 5,165,560 A | 11/1992 | Enniss, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,380,295 A | 1/1995 | Vacca |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| 5,829,589 A | 11/1998 | Nguyen et al. |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,375,640 B1 | 4/2002 | Teraoka |
| 6,394,983 B1 | 5/2002 | Mayoral et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanley et al. |
| 6,775,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,055,273 B2 | 6/2006 | Roshkoff |
| 7,125,397 B2 | 10/2006 | Woehr et al. |
| 7,141,286 B2 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |

(56) References Cited

U.S. PATENT DOCUMENTS

| | | |
|---|---|---|
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,443,999 B1 | 5/2013 | Reinders |
| D684,057 S | 6/2013 | Kwon |
| 8,512,277 B2 | 8/2013 | Del Vecchio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 | 10/2014 | Vitello |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,082,157 B2 | 7/2015 | Gibson |
| 9,101,534 B2 | 8/2015 | Bochenko |
| D738,495 S | 9/2015 | Strong et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 3/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello |
| D815,945 S | 4/2018 | Fischer et al. |
| 9,987,438 B2 | 6/2018 | Stillson |
| D825,746 S | 8/2018 | Davis et al. |
| 10,039,913 B2 | 8/2018 | Yeh et al. |
| D831,201 S | 10/2018 | Holtz et al. |
| D820,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,376,655 B2 | 8/2019 | Pupke et al. |
| D859,125 S | 9/2019 | Weagle et al. |
| 10,758,684 B1 | 9/2020 | Vitello et al. |
| 2001/0034506 A1 | 10/2001 | Hirschman |
| 2001/0056258 A1 | 12/2001 | Evans |
| 2002/0007147 A1 | 1/2002 | Capes et al. |
| 2002/0023409 A1 | 2/2002 | Py |
| 2002/0097396 A1 | 7/2002 | Schafer |
| 2002/0099334 A1 | 7/2002 | Hanson |
| 2002/0101656 A1 | 8/2002 | Blumenthal |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse |
| 2007/0219503 A1 | 9/2007 | Loop |
| 2007/0257111 A1 | 11/2007 | Ortenzi |
| 2008/0068178 A1 | 3/2008 | Meyer |
| 2008/0097310 A1* | 4/2008 | Buehler ............ A61M 5/50 604/111 |
| 2008/0106388 A1 | 5/2008 | Knight |
| 2008/0140020 A1 | 6/2008 | Shirley |
| 2008/0243088 A1 | 10/2008 | Evans |
| 2008/0306443 A1 | 12/2008 | Neer |
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |

(56) References Cited

U.S. PATENT DOCUMENTS

| | | |
|---|---|---|
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |
| 2014/0000781 A1 | 1/2014 | Franko, Jr. |
| 2014/0034536 A1 | 2/2014 | Reinhardt et al. |
| 2014/0069202 A1 | 3/2014 | Fisk |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin |
| 2014/0353196 A1 | 12/2014 | Key |
| 2015/0182686 A1 | 7/2015 | Okihara |
| 2015/0191633 A1 | 7/2015 | De Boel et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan |
| 2017/0173321 A1 | 6/2017 | Davis et al. |
| 2017/0203086 A1 | 7/2017 | Davis |
| 2017/0319438 A1 | 11/2017 | Davis et al. |
| 2017/0354792 A1 | 12/2017 | Ward |
| 2018/0001540 A1 | 1/2018 | Byun |
| 2018/0078684 A1 | 3/2018 | Peng et al. |
| 2018/0089593 A1 | 3/2018 | Patel et al. |

\* cited by examiner

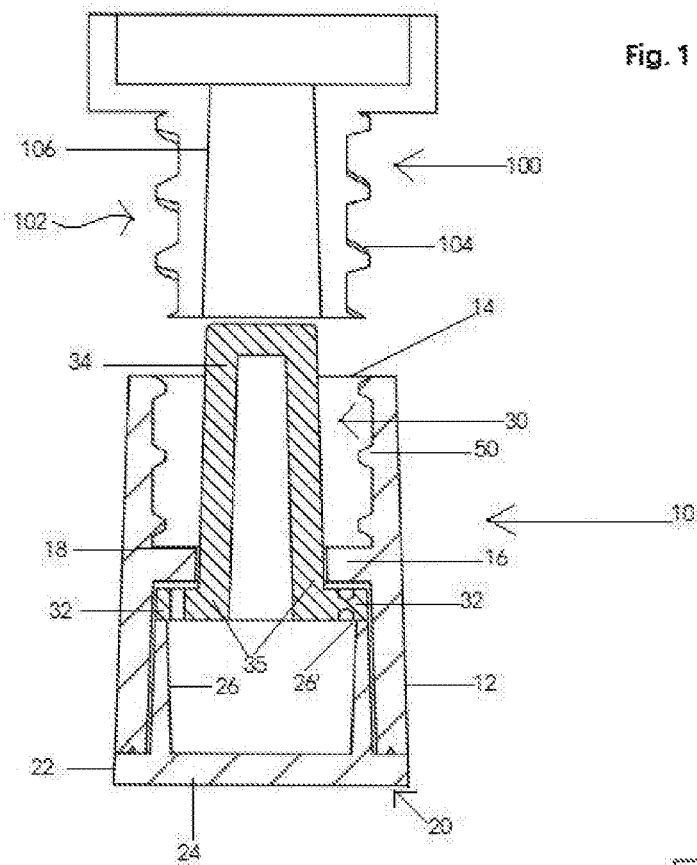
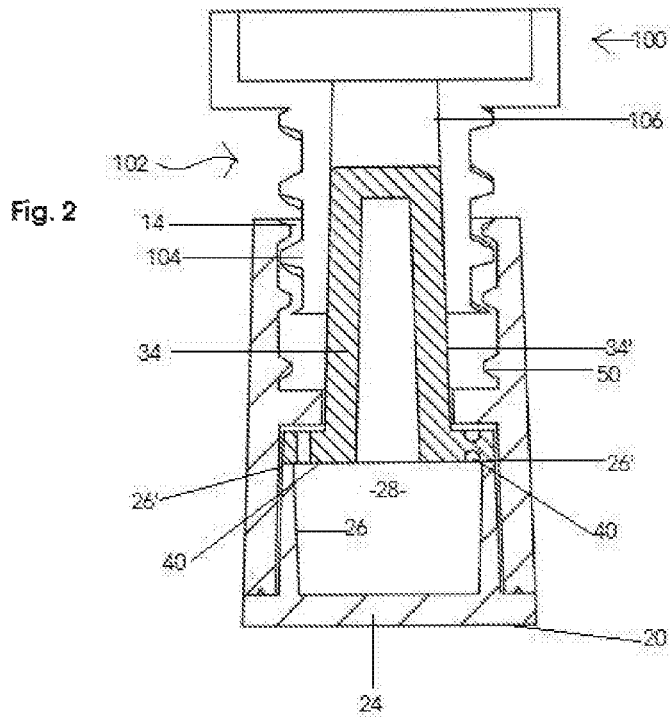

TAMPER EVIDENT CLOSURE ASSEMBLY FOR A MEDICAL DEVICE

CLAIM OF PRIORITY

The present application is based on and a claim of priority is made under 35 U.S.C. Section 119(e) to a provisional patent application that is currently in the U.S. Patent and Trademark Office, namely, that having Ser. No. 62/482,490 and a filing date of Apr. 6, 2017, and which is incorporated herein by reference.

BACKGROUND OF THE INVENTION

Field of the Invention

This invention is directed to a single use closure assembly for a medical device having tamper evident capabilities and including a housing and a tip cap disposed in a captured orientation or retained position therein. Exertion of a predetermined force on the tip cap, concurrent to attachment to the medical device, will dispose a portion of the tip cap out of the captured orientation and into the retained position, wherein the tip cap remains in flow restricting engagement with the medical device in the retained position, until the medical device is disconnected from the housing.

Description of the Related Art

In the medical field, it is a relatively common procedure for authorized medical personnel to order a drug or medication which is to be administered by injection or other procedures, including by intravenous (IV) infusion. It is also relatively common procedure for a number of medical administering or dispensing devices to be pre-loaded or filled, whether within the hospital or at another facility and location, which may be generally referred to as a filling station. However, such filling stations may be located in a remote part of the facility, relative to the patient care area where the medication to be administered.

Because of the remote location of many nurse's stations, relative to filling stations, a fluid or drug loaded medical device is often given to other personnel for delivery to a nurse's station. Also, in situations where an expensive or addictive drug that has been loaded in the medical device, there is an increased danger that attempts will be made to access the contents of the pre-loaded device by unauthorized personnel. This possibility can present a danger of substituting the preloaded medication with a saline or other fluid. By way of example, if a saline solution was substituted for a dose of morphine, the result could be extremely serious.

Thus, there is a problem of knowing if a sealed, preloaded syringe or other administering device has, or has not, been compromised by contamination, unauthorized substitution or other types of tampering. This and related types of problems have been described in one or more previously granted U.S. patents to one of the inventors herein, such as U.S. Pat. No. 5,328,474.

In addition to the administration of drugs, medicine, etc., meaningful protection is required in the use of enteral feeding sets, like medical devices and accessories. As commonly recognized in the medical and related professions, the term "enteral" relates to the administration or removal of fluid in the form of liquid or gas to or from the gastrointestinal tract. Moreover, enteral connectors and/or fixtures of the type referred to herein relate to medical devices or accessories which are intended for use in enteral applications.

Also, with regard to administering fluids to a patient by intravenous (IV) infusion, a variety of IV assemblies are known and are useful in the treatment of a number of medical conditions, as a variety of fluids and/or medicines can be administered to a patient utilizing such assemblies over a prescribed period of time and in controlled amounts. In use, a conventional IV administration assembly typically includes a reservoir or container, in the form of a bottle or flexible material bag, disposed in an elevated, suspended location substantially adjacent to the patient being treated. In addition, the IV fluid flows from the supported and elevated IV bag to the patient by means of elongated, flexible tubing connected at a proximal end to the IV bag and at the other distal end, connected intravenously to the patient by way of a catheter or like structure.

In periods of non-use, it is important to maintain closures of the type set forth herein in a closed and fluid sealed and/or flow restricting attachment to preloaded medical devices in order to maintain the sterility and integrity of the contents of a preloaded medical device, prior to use.

Therefore, regardless of the known or conventional attempts to provide a flow restricting closure having tamper evident capabilities structured to protect the contents of preloaded administering devices, certain problems still remain in this field of art. Accordingly, there is a need in this area for an improved, closure assembly which provides a secure and reliable flow restricting or sealing connection to the discharge port or fixture of a medical device such as, but not limited to, a female connector. If any such improved closure assembly were developed, it should also have tamper evident capabilities operative to provide a clear and reliable indication that use and/or attempted tampering with the medical dispensing device has occurred.

Further, if any such improved closure assembly were developed, it should also be capable of use, with little or no structural modification, with a variety of different medical administering or dispensing devices. Also, it may be beneficial and advantageous that any such improved closure assembly be structured for a single use application, thereby further providing an indication of prior use or tampering. Finally, any such improved closure assembly should also be structurally and operatively reliable, while still remaining cost effective to manufacture and assemble, in order to facilitate widespread use and acceptance throughout the medical profession.

SUMMARY OF THE INVENTION

The present invention is directed to a closure assembly for a medical device such as a medical dispensing or administering device including, but not limited to, a prefilled syringe. The structural and operative features of the one or more embodiments of the closure assembly include tamper evident capabilities and its intended application as a single use device.

More specifically, the closure assembly includes a housing having an access opening preferably formed at one end thereof and disposed in accessible, communicating relation with an at least partially hollow interior of the housing. A stop member is integrally or otherwise fixedly connected to interior portions of the housing and an end cap is connected in at least partially closing or covering relation to an end of the housing, which may be oppositely disposed to the access opening.

A tip cap is disposed within the hollow interior of the housing and includes a base and a flow restrictor. The flow restrictor is at least initially connected to the base but is detachable therefrom under certain operative conditions. In turn, the base is disposed within the housing in a "captured orientation", between the stop member and a correspondingly disposed portion of the end cap. Moreover, in at least one embodiment, the "captured orientation" of the base may be further defined by the base not being directly attached or connected to interior portions of the housing and being loosely disposed between the stop member and the end cap.

In addition, the captured orientation may be further defined by a portion of the end cap being at least partially disposed in a supporting, retaining engagement with the base of the p cap. Such cooperative structuring between the base and a retaining portion of the end cap facilitates the aforementioned captured orientation as well as a disconnection of the flow restrictor from the base, as described in greater detail hereinafter. Moreover, the fact that the base is not directly attached or connected to the interior of the housing, when in the captured orientation, significantly facilitates the manufacture and assembling of the closure assembly in a time-saving, cost effective manner. As such, the need to weld, mold or otherwise connect the base directly to interior portions of the housing is eliminated. Therefore, when assembling the closure assembly, the tip cap, and in particular the base, may be manually or mechanically placed within the housing in the intended position, relative to the stop member and end cap.

In contrast to the base, and as indicated above, the flow restrictor of the tip cap is removably connected to the base and as such is not fixed within the housing. Therefore, in at least one preferred embodiment, the tip cap includes a frangible or other type of removable connection disposed in removable interconnecting relation between the base and a corresponding and/or contiguous portion of the flow restrictor. The frangible or other type of removable connection between the base and the flow restrictor is specifically structured to break or fail upon a predetermined force being applied to the flow restrictor. As set forth in detail hereinafter, such a predetermined force will be applied to the flow restrictor concurrent to the attachment of the housing to the medical device, with which it is used.

In more specific terms, the housing includes a connecting structure preferably, but not necessarily, a threaded connecting structure formed on the interior surface of the housing and preferably extending along at least a majority of the length thereof from the access opening to the stop member. The connecting structure and/or threaded connecting structure is cooperatively structured and dimensioned with the connecting structure on the medical device to establish the aforementioned rotational attachment of the housing to the medical device. Similarly, the aforementioned connecting structure and/or threaded connecting structure will facilitate the intended administering use of the medical device by a rotational detachment of the housing from the medical device.

As a result, a rotational attachment, including a rotational threaded attachment, of the housing on the medical device results in a flow restricting engagement of the flow restrictor with a discharge port or other discharge structure on the medical device. In turn, such a flow restricting engagement will result and be at least partially defined by an interacting engagement, such as an interacting frictional and/or resistance engagement, between the outer surface of the flow restrictor and corresponding surface, such as an inner surface of the cooperatively configured connecting structure associated with the discharge port or discharge structure of the medical device. Further, such interacting engagement between the above-noted corresponding surfaces will result in a force being exerted on the flow restrictor, as the housing is being rotationally attached and/or threaded onto the medical device. Upon a predetermined degree of force being exerted on the flow restrictor, while the housing is being rotationally attached to the medical device, the flow restrictor will be detached from the base. As indicated, such a detachment of the flow restrictor from the base will be the result of an intended failure or breakage of the frangible or other type removable interconnection between the base and a correspondingly disposed portion of the flow restrictor.

However, the aforementioned interacting frictional or resistance engagement between the flow restrictor and the discharge port or discharge structure of the medical device will be sufficient to maintain the flow restrictor in flow restricting engagement with the medical device, even when the flow restrictor is detached from the base. In addition, the flow restrictor will be disposed in a "retained position" within the housing when disconnected from the base and, whether or not the flow restrictor is disposed in flow restricting relation to the medical device. For purposes of clarity, the term "retained position" is used herein to describe the flow restrictor being disconnected or detached from the base and being disposed into or out of flow restricting relation to the medical device. Also, the "retained position" of the flow restrictor may also be defined by at least a portion of the flow restrictor disposed within the interior of the housing between the end cap in the stop member.

Further, the stop member will be structured and disposed within the housing in removal restricting relation to the flow restrictor. In more specific terms, the stop member will be disposed in interruptive relation to passage of at least a portion of the flow restrictor out of the housing, through the access opening. Therefore, such an interruptive, removal restricting disposition of the stop member, relative to the flow restrictor, will prevent removal of the flow restrictor from the interior of the housing, through the access opening.

As described in greater detail hereinafter, the aforementioned interacting frictional and/or resistance engagement is facilitated by structuring of the flow restrictor to include an outwardly converging tapered configuration. Such a tapered configuration may also be defined by the flow restrictor comprising a plug in the form of a male Lure connector. In cooperation therewith, the connector associated with the discharge structure of the medical device may be the form of a female Luer connector. As a result, disposition of the male lure connector in flow restricting relation within the female Luer connector of the discharge port will result in the interacting engagement between the correspondingly disposed outer tapered surfaces thereof.

As indicated, such interacting engagement, which at least partially defines the flow restricting engagement between the housing in the medical device, is established as the housing is attached to the medical device and is maintained, after detachment of the flow restrictor from the base. Moreover, the provision of a threaded or like connecting structure within the housing being disposed in mating engagement with a cooperatively dimensioned and disposed connecting structurer on the medical device, will force the aforementioned tapered surfaces into the interacting engagement with one another. As the housing continues to be rotationally attached or "threaded" onto the medical device, a force will be exerted on the flow restrictor. Therefore, the maintaining of the flow restrictor in flow restricting relation to the discharge structure of the medical device, even upon disconnection of the flow restrictor with the base, is accomplished and at least partially dependent on the dimension, structure and configuration of a male configured flow restrictor and a cooperatively dimensioned female configured connector (discharge port) on the medical device.

As generally indicated above, once the flow restrictor is detached from the base, the maintenance of the flow restrictor in a retained position within the housing is accomplished by a cooperative positioning, dimensioning and structuring of the stop member and at least a portion of the flow restrictor. More specifically, the stop member is integrally or otherwise fixedly connected to the interior surface or other interior portions of the housing. Further, in at least one embodiment, the stop member extends outwardly from the interior surface to which it is connected, inwardly towards a center area of the housing. As a result, a passage or opening will be provided in the stop member and/or between the stop member and an interior portion of the housing. Such opening or passage is dimensioned to allow disposition of the flow restrictor at least partially there through, so as to be readily accessible by the medical device entering the housing through the access opening.

However, at least a portion of the flow restrictor, such as that portion removably connected to the base, is dimensioned and/or configured to not pass through or beyond the stop member. As a result, the entirety of the flow restrictor will not be able to pass beyond the stop member, such as through the open area of the stop member, towards the access opening. Therefore, the stop member can be accurately described as being disposed in a removal restricting relation and/or interruptive relation to passage of the flow restrictor from the interior of the housing through to the access opening. Accordingly, the flow restrictor will be maintained in the "retained position" within the interior of the housing when detached from the base and also when the housing is disconnected from the medical device.

Additional structural d operative features of at least one embodiment of the closure assembly include the end cap having a retaining member or structure and an at least partially open interior. As such, the retaining structure will extend into the interior of the housing and be disposed in supporting, at least partially capturing engagement with the base of the tip cap. Such supporting engagement will at least partially define the captured orientation of the base, between the retaining portion of the end cap and stop member. Upon disconnection of the flow restrictor from the base, and detachment of the housing from the medical device, the flow restrictor may "fall", such as by gravity, or otherwise be disposed into the retained position, within the open interior of the end cap.

As indicated herein, the closure assembly of the present invention may be structured to be a single use device. This is accomplished by disposition of the flow restrictor into the retained position within the interior of the housing or within the open interior of the end cap, after detachment of the housing from the medical device. Accordingly, when the flow restrictor is in the retained position, it will not be able to be sufficiently accessed or engaged by the medical device to accomplish a fluid restricting connection therebetween. More specifically, an attempt to reuse the closure assembly, after once having been detached from the medical device, may result in the discharge port thereof being reinserted through the access opening concurrent to the corresponding connecting structures of the medical device and the closure assembly being reattached, such as by the aforementioned rotational threaded attachment therebetween.

However, as the connecting structure of the medical device advances into the interior of the housing it will eventually engage the aforementioned stop member. The location of the stop member within the housing will prevent the discharge port or discharge structure thereof from engaging the flow restrictor and prevent establishment of the aforementioned interacting engagement between the corresponding surfaces of the discharge port and flow restrictor. The flow restrictor is freely movable, once having been detached from the medical device and being in the retained position. Therefore, there will not be a sufficiently stable positioning of the flow restrictor to accomplish the interacting engagement with the connecting structures of the medical device and the flow restrictor. Accordingly, while the housing may be reconnected to the medical device by the aforementioned rotational attachment, the flow restrictor will remain freely movable in the retained position out of a sufficiently accessible location to be connected in flow restricting engagement with the medical device. This inability to "reuse" the closure assembly in the intended flow restricting manner will be at least one indicator of tampering or actual authorized use.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 is a longitudinal sectional view representing interior portions of the closure assembly of the present invention prior to intended attachment to a medical device.

FIG. 2 is a longitudinal sectional view of the embodiment of FIG. 1 representing the closure assembly being rotationally attached to the medical device.

Like reference numerals refer to like parts throughout the several views of the drawings.

DETAILED DESCRIPTION OF THE PREFERRED EMBODIMENT

As represented in the accompanying Figures, the present invention is directed to a closure assembly, generally indicated as 10, for a medical device such as a medical dispensing or administering device including, but not limited to, a prefilled syringe 100. The structural and operative features of the one or more embodiments of the closure assembly 10 include tamper evident capabilities and its intended application as a single use device. It is further emphasized that while the closure assembly 10 is represented herein for use with a prefilled syringe 100, it can also be used in the intended manner to establish a flow restricting connection with a variety of other medical administering or dispensing devices.

Figure 3:
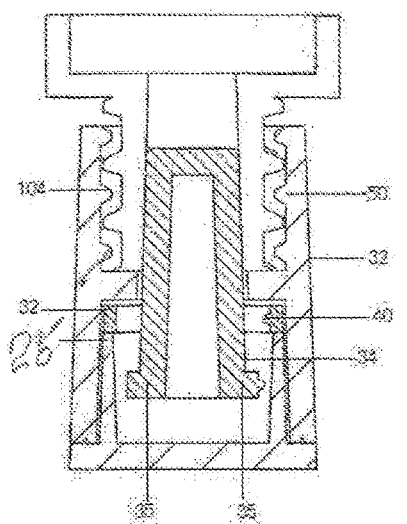
FIG. 3 is a longitudinal sectional view of the embodiment of FIGS. 1-2 representing a secure attachment of the closure assembly in flow restricting relation to the medical device.
Figure 4:
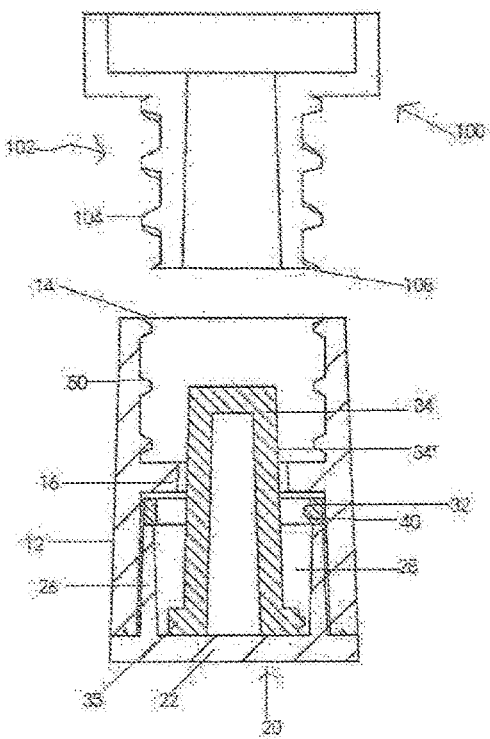
FIG. 4 is a longitudinal sectional view of the embodiment of FIGS. 1-3 representing a disconnection of the closure assembly from the medical device, after a flow restricting engagement had been established therebetween.
Figure 5:
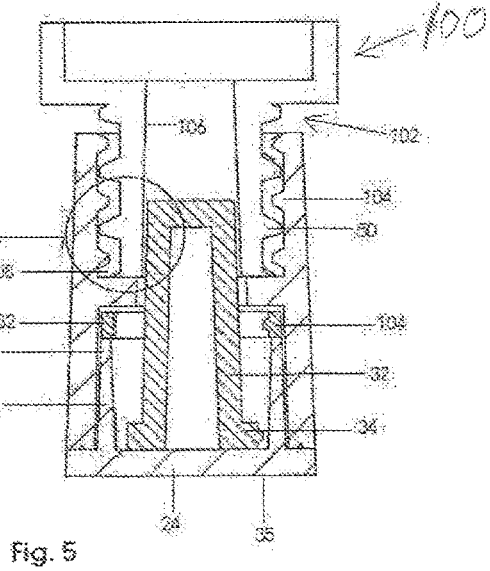
FIG. 5 is a longitudinal sectional view of the embodiment of FIGS. 1-4 wherein the closure assembly is reattached to the medical device for an attempted reuse of the closure assembly.
Figure 5A:
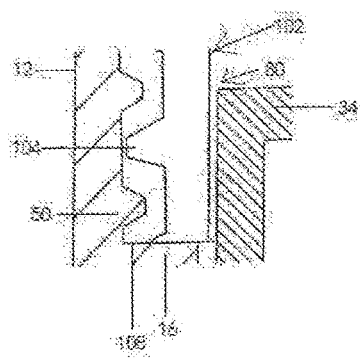
FIG. 5A is a detail view in partial cutaway and section of the highlighted structure "A" of FIG. 5.

For purposes of clarity, and to facilitate the understanding of the structural and operative features of the closure assembly 10, the included Figures provide a substantially sequential representation of at least one exemplified use of the closure assembly 10. As such, FIG. 1 represents the closure assembly in its initial assembled state prior to attachment to the medical device 100. FIG. 2 represents the embodiment of FIG. 1 wherein the closure assembly 10 is in its initially assembled state and while beginning attachment to the medical device 100. FIG. 3 represents the closure assembly 10 attached in flow restricting engagement with the medical device 100. FIG. 4 represents the closure assembly 10 having been disconnected from the medical device 100 and a resultant change in the position of structural components of the closure assembly 10. FIGS. 5-5A represent an attempted reuse of the closure assembly 10 through reattachment to the medical device 100.

With initial reference to FIG. 1, the closure assembly 10 includes a housing 12 having an access opening 14 aligned or otherwise disposed in accessible, communicating relation with at least a portion of an interior of the housing 12. In addition, the access opening 14 is disposed and dimensioned to allow receipt there-through of a discharge port 106 or discharge structure generally indicated as 102 of the medical device 100, as represented in at least FIGS. 2-3. The housing 12 further includes stop member 16 integrally or otherwise fixedly connected to interior portions of the housing 12. Further, the stop member 16 may extend inwardly towards a substantially central interior of the housing 12 from the interior portions of the housing 12 to which it is connected. In addition, the stop member 16 may be configured to at least partially define an opening or passage 18, which may or may not be centrally located.

The housing 12 also includes an end cap 20 which may be connected in at least partially closing or covering relation to an end 22 of the housing 12. As further represented, the end cap may be substantially oppositely disposed to the access opening 14 and be located on the opposite side of the stop member 16 relative to the access opening 14. The end cap 20 may be fixedly attached by welding or other appropriate techniques in its intended closing or covering position relative to the end 22 of the housing 12. Further, the end cap 20 may include an end cap base 24 and a retaining structure 26 cooperatively disposed and structured relative to the stop member 16, as described in greater detail hereinafter.

Still referring to FIG. 1, a tip cap generally indicated as 30 is disposed within the housing 12 and includes a base 32 and a flow restrictor 34, The flow restrictor 34 is removably connected to the base 32 at least initially before attachment of the housing 12 to the medical device 100. In turn, the base 32 is disposed within the housing in a "captured orientation", as represented in FIGS. 1-5. The captured orientation of the base 32 comprises it being disposed between the stop member 16 and an interior end 26' of the retaining structure 26 of the end cap 20. Moreover, the "captured orientation" of the base 32 may be further defined by the base 32 not being directly attached or connected to interior portions of the housing 12. Also, at least one embodiment of the closure assembly 10 of the present invention defines the captured orientation of the base 32 as being loosely and/or even at least minimally movable between the retaining structure 26 and the stop member 16.

In order to facilitate the intended operative features of the closure assembly 10 including, but not limited to, an intended disconnection of the flow restrictor 34 from the base 32, the "captured orientation" may be further defined by inner end portion 26' of the retaining structure 26, being disposed in at least partially capturing engagement with a corresponding side or surface of the base 32, as clearly represented throughout the Figures. Moreover, the fact that the base 32 is not directly attached or connected to the interior of the housing 12 and may be loosely disposed, when in the "captured orientation", significantly facilitates the manufacture and assembling of the closure assembly 10 in a time-saving, cost effective manner. Such positioning and structuring of the base 32 eliminates the need to weld, mold or otherwise directly connect the base 32 to interior portions of the housing 12. As such, when assembling the closure assembly 10, the tip cap 30 may be manually or mechanically placed within the housing 12 in the intended position represented in at least FIGS. 1 and 2, relative to the stop member 16 and/or end cap 20.

In contrast to the base 32, and as indicated above, the flow restrictor 34 of the tip cap 30 is removably connected to the base 32 and as such, is not fixed within the housing 12. Therefore, in at least one preferred embodiment of the closure assembly 10, the tip cap 30 includes a frangible or other type of removable connection 40, disposed in removable interconnecting relation between the base 32 and a corresponding and/or contiguous portion 35 of the flow restrictor 34. Further, the frangible or other type of removable connection 40 is intentionally structured to break or fail upon a predetermined force being applied to the flow restrictor 34. As set forth in detail hereinafter, such a predetermined force will be exerted on the flow restrictor 34 concurrent to the flow restrictor 34 being attached in flow restricting relation with the medical device 100, as the housing 12 is being connected to the medical device 100.

In more specific terms, the housing 12 includes a connecting structure 50 preferably, but not necessarily, in the form of a threaded connecting structure formed on the interior surface of the housing 12, and preferably extending continuously along at least a majority of the length thereof, between the access opening 14 and the stop member 16. The connecting structure and/or threaded connecting structure 50 is cooperatively structured, dimensioned and configured with the connecting structure 104 of the medical device 100, which may also be a threaded connecting structure. As represented, the connecting structure 104 of the medical device is formed on an outer portion of the discharge port 106, which is part of the discharge structure 102 of the medical device 100. This cooperative structuring between the connecting structure 50 of the housing 12 and the connecting structure 104 of the medical device 100 facilitates a rotational attachment of the housing 12 to the medical device 100. Similarly, the cooperatively structured connecting structures 50 and 100 will also facilitate a quick and easy use of the medical device 100 by facilitating a rotational detachment of the housing 12 from the discharge structure 102 and discharge port 106 of the medical device 100, as represented in FIG. 4.

As represented in FIGS. 2 and 3, the attachment of the housing 12 on the medical device 100 results in a flow restricting engagement of the flow restrictor 34 within the discharge port 106 of the discharge structure 102. In turn, such a flow restricting engagement will result in and be at least partially defined by an "interacting engagement" between the outer surface 34' of the flow restrictor 34 and an inner surface of the discharge port 106, of the discharge structure 102. Further, such interacting engagement will occur substantially concurrent to a force being exerted on the flow restrictor 34, as the housing 12 is being rotationally attached and/or threaded onto the cooperative connecting structure 104.

The interacting engagement, which may be frictional, is facilitated by structuring of the flow restrictor 34 to include an outwardly converging tapered configuration. Such a tapered configuration may also be defined by the flow restrictor 34 comprising a plug in the form of a male Lure connector. In cooperation therewith, the discharge port 106 may serve as a connector of the medical device 100 and may be the form of a female Luer connector. As a result, disposition of the male lure connector (flow restrictor 34) in flow restricting relation within the female Luer connector (discharge port 106) will result in and be at least partially defined by the aforementioned interacting engagement between the correspondingly disposed outer and inner tapered surfaces of the flow restrictor 34 and discharge port 106, respectively. In turn, the interacting engagement will result in the exertion of a force on the flow restrictor during the attachment of the housing 12 to the medical device 100.

In more specific terms, a force will be exerted on the flow restrictor 34, due at least in part to the aforementioned interacting engagement between the outer surface 34' and the inner surface of the discharge port 106. Such force will be exerted on the flow restrictor 34 while the housing 12 is being rotationally attached to the medical device 100, as also represented in FIG. 3. When the force exerted on the flow restrictor 34 reaches a predetermined level or degree, the flow restrictor 34 will be at least minimally displaced, as represented in FIG. 3. Such a displacement will be sufficient to result in detachment of the flow restrictor 34 from the base 32. As indicated, such a detachment of the flow restrictor 34 from the base 32 will be based on an intended failure or breakage of the frangible or other type removable interconnection 40, when the force exerted on the flow restrictor 34 is sufficient to accomplish such intended failure. It is emphasized that the amount of force required to detach the flow restrictor 34 or portion 35 from the base 32 may vary. The variance of such a predetermined disconnecting force may be dependent, at least in part, on the overall dimension, configuration and/or structuring of the various parts of the closure assembly 10, as well as the type and structuring of the medical device 100 including, hut not limited to, the connecting structures 50, 104 and discharge port 106 and flow restrictor 34.

With primary reference to at least the sequentially representative FIGS. 1-3, the closure assembly 10 includes an initially structured assembly of parts prior to attachment to the medical device 100, as represented in FIG. 1. FIG. 2 represents the housing 12 beginning its attachment to the medical device 100. In doing so, the connecting structure 104 and discharge port 106 passes through the access opening 14 and begins its rotational and/or rotational threaded attachment to the connecting structure 50. As the result of such a continued rotational attachment, the discharge port 106 will be advanced inwardly into the housing 12 towards and into an eventual engagement with the flow restrictor 34. In turn, the outer surface 34' will move into interacting engagement with the interior of the discharge port 106. Upon a continued rotational and axial advancement of the flow restrictor 34 into the discharge port 106, the interacting engagement between the outer surface 34' an inner surface of the discharge port 106 will "tighten".

With further regard to FIG. 3, this tightening and/or increased resistance will result in an increased force being exerted on the flow restrictor 34. This increased force will eventually be sufficient to break the removable connection 40 between the base 32 and portion 35 of the flow restrictor 34. The flow restrictor 34 will thereby be at least minimally displaced from its initial assembled position, as represented in FIG. 1. This displacement will result in the aforementioned detachment of the flow restrictor 34 from the base 32. However, due to the aforementioned interacting engagement between the outer surface 34' in the interior of the discharge port 106, the flow restrictor 34 will remain in flow restricting relation within the discharge port 106, as represented in FIG. 3. Therefore, as indicated, the flow restrictor 34 will be maintained in the intended flow restricting relation to the medical device 100, even when the flow restrictor 34 is detached from the base 32. This flow restricting engagement of the flow restrictor 34, relative to the discharge port 106, will be maintained until the medical device 100 is "unthreaded" or rotationally detached from the housing 12, as represented in FIG. 4 and described in detail hereinafter.

Once the flow restrictor 34 is disconnected from the base 32, it will be disposed in a "retained position" within the housing 12 as clearly represented in FIGS. 3 and 4. For purposes of clarity, the term "retained position" is used herein to describe the flow restrictor 34 being disconnected or detached from the base 32 and having at least a portion thereof disposed within an interior portion of the housing 12 in an area between the stop member 16 and the end cap base 24. It is to be noted that the flow restrictor 34 may assume the retained position when it is disposed in flow restricting engagement with the discharge port 106, as represented in FIGS. 2-3, and also when it is removed from the flow restricting engagement with the discharge port 106, as represented in FIG. 4.

By way of example, the flow restrictor 34 is represented as being disposed in the flow restricting engagement with the discharge port 106 in at least FIG. 3. However, a portion 35 thereof is detached from the base 32 and is disposed within the housing 12, between the stop member 16 and the end cap base 24. Therefore, FIG. 3 is also representative of the flow restrictor 34 being in the aforementioned "retained position". In contrast, FIG. 4 represents the flow restrictor 34 being removed from its flow restricting engagement with the discharge port 106 as the housing 12 is entirely disconnected from the medical device 100.

In more specific terms, as the housing 12 is rotationally detached or unthreaded from the medical device 100, the flow restrictor 34 will at least initially move with the discharge port 106 due to the interacting engagement between corresponding surfaces thereof, as set forth above. However, eventually the portion 35 of the flow restrictor 34 will come into interruptive engagement with the stop member 16. Thereafter, a continued rotational detachment of the housing 12 will result in a further separation of the flow restrictor 34 from the discharge port 106, while the stop member 16 is in interruptive engagement with the portion 35. This continued separation of the housing 12 from the medical device 100 will result in a disconnection of the previously established flow restricting engagement between the flow restrictor 34 and the discharge port 106. Due to the fact that the flow restrictor 34 is then the freely movable within the interior of the housing 12, it will fall, drop or otherwise be disposed back into the interior of the housing 12 or open interior 28 of the end cap 20 and thereby remain in its "retained position" as clearly represented in FIG. 4.

As should be apparent, once the flow restrictor 34 is detached from the base 32, the maintaining of the flow restrictor 34 in a retained position within the housing 12 is accomplished by a cooperative positioning, dimensioning and structuring of the aforementioned stop member 16 and at least the portion 35 of the flow restrictor 34. As indicated herein, the stop member 16 is integrally or otherwise fixedly connected to the interior portions of the housing 12 and extends outwardly from the interior surface to which it is connected and inwardly towards a center area of the housing 12. As a result, the passage or opening 18 is defined. The opening or passage 18 is dimensioned to allow disposition of the flow restrictor 34 at least partially there through, so as to be readily accessible by the medical device 100 entering the housing 12 through the access opening 14.

However, at least the portion 35 of the flow restrictor 34, previously connected to the base 32, is dimensioned and/or configured to prevent its passage through or beyond the stop member 16. Accordingly, the entirety of the flow restrictor 34 will not be able to pass beyond the stop member the 16, such as through the open area 18, towards the access opening 14. Therefore, the stop member 16 can be accurately described as being disposed in a "removal restricting" relation to the flow restrictor 34, relative to the access opening 14. The flow restrictor 34 will thereby be maintained in the aforementioned and described "retained position" within the interior of the housing 12, below the stop member 16, when detached from the base 32 and also when the housing 12 is rotationally detached from the medical device 100, as represented in FIG. 4.

Additional structural and operative features of at least one embodiment of the closure assembly 10 includes the retaining structure 26 being in the form of a skirt having an at least partially curvilinear configuration and being disposed at least partially in surrounding relation to the open interior area 28. As such, the retaining structure or skirt 26 extends from the base 24 of the end cap 20 inwardly into the interior of the housing 12, wherein the end portion 26' of the retaining skirt 26 is disposed in supporting, at least partially capturing engagement with the base 32.

As indicated herein, the closure assembly 10 of the present invention may be structured to be a single use device. As represented in FIGS. 4, 5-5A when the flow restrictor 34 is in the retained position of FIG. 4, concurrent to being disconnected from the base 32 and from the medical device 100, the flow restrictor 34 will not be able to be sufficiently accessed to reestablish a flow restricting connection with a medical device 100. More specifically, if a medical device 100 is reinserted through the access opening 14, the cooperative disposition and structure of the connecting structures 50 and 104 of the housing 12 and the discharge structure 102, respectively, will allow a rotational re-attachment of the housing 12 to the medical device 100.

However, as the connecting structure 104 and discharge port 106 are advanced into the interior of the housing 12, an end or other correspondingly disposed portion 108 of the connecting structure 104 will eventually engage the stop member 16, as represented in FIGS. 5 and 5A. The connecting structure 104 and discharge port 106 will thereby be prevented from advancing into a connecting relation with the flow restrictor 34. As a result, a flow restricting engagement with the flow restrictor 34 will not be able to be accomplished.

In addition, because the flow restrictor 34 is in the retained position of FIG. 4 and is freely movable within the housing 12 and/or open interior 28 of the end cap 20, there will not be sufficient resistance on the flow restrictor 34 to allow rotational engagement therewith by the medical device. In more specific terms, once the flow restrictor 34 is in the retained position represented in FIG. 4, being disconnected from the medical device 100, a spacing 80, as represented in FIG. 5A, will exist and be maintained between the tapered surfaces of the flow restrictor 34 and the discharge port 106, as the flow restrictor 34 is advanced into the discharge port 106. In that the connecting structure 104 and part 108 thereof cannot be further advanced beyond the stop member 16, the spacing 80 will be maintained. The existence of the spacing 80 will prevent the aforementioned interacting frictional engagement between the tapered surfaces of the flow restrictor 34 of the discharge port 106. Therefore, while the housing 12 may be reconnected to the medical 100 by the aforementioned rotational threaded attachment, the flow restrictor 34 will remain unconnected and unattached in the retained position of FIG. 4. This inability to "reuse" the closure assembly in the intended flow restricting manner will be at least one indicator of tampering or actual authorized use.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A closure assembly for a medical device, said closure assembly comprising:
    a housing having an access opening and a stop member disposed within said housing,
    an end cap connected in at least partially covering relation to one end of said housing substantially opposite to said access opening,
    a tip cap including a base and a flow restrictor; said flow restrictor removably connected to said base,
    said base disposed in a captured orientation between said stop member and said end cap,
    said end cap including a retaining member disposed within said housing in supporting, at least partially capturing engagement with said base,
    said retaining member comprising an elongated skirt disposed in at least partially surrounding relation to an open interior of said end cap,
    said flow restrictor is at least partially disposed in a retained position within said open interior of said end cap, subsequent to disconnection from said base, concurrent to a predetermined force applied to said flow restrictor.

2. The closure assembly as recited in claim 1 wherein said captured orientation further comprises said base movable between said stop member and said end cap.

3. The closure assembly as recited in claim 1 wherein said housing further comprises a connecting structure; said connecting structure disposed and cooperatively structured with the medical device to define a rotational attachment and a rotational detachment of said housing onto and from the medical device, said flow restrictor disposed in said retained position within said housing concurrent to said rotational detachment.

4. The closure assembly as recited in claim 3 wherein said connecting structure comprises a threaded connecting structure formed on and extending along at least a majority of a length of an interior surface of said housing between said access opening and said stop member.

5. The closure assembly as recited in claim 3 wherein said rotational attachment is determinative of said predetermined force being applied to said flow restrictor.

6. The closure assembly as recited in claim 3 wherein said flow restrictor is disposed in a flow restricting relation to the medical device substantially concurrent to said rotational attachment and subsequent to disconnection of said flow restrictor from said base.

7. The closure assembly as recited in claim 1 wherein said stop member is disposed in a removal restricting relation to said flow restrictor, relative to said access opening.

8. The closure assembly as recited in claim 1 wherein said flow restrictor comprises a plug member including an outer surface having a tapered, converging configuration extending substantially from said base toward said access opening.

9. The closure assembly as recited in claim 1 wherein said flow restrictor is at least partially disposed in a retained position within said open interior of said end cap, subsequent to disconnection of said housing from said medical device.

10. A closure assembly for a medical device, said closure assembly comprising:
- a housing including an end cap, an access opening and a stop member disposed within said housing,
- a retaining member disposed within said housing in at least partially surrounding relation to an open interior of said end cap,
- a tip cap including a base and a flow restrictor, said flow restrictor removably connected to said base,
- said stop member disposed in a removal restricting relation to said flow restrictor, relative to said access opening,
- said base disposed in a captured orientation between said stop member and said retaining member; said captured orientation comprising said base disposed in an unattached relation to interior portions of said housing,
- said flow restrictor disposed in a retained position within said housing; said retained position comprising said flow restrictor disconnected from said base, substantially concurrent to disposition thereof in a flow restricting relation to the medical device,
- said flow restrictor disposed in said flow restricting relation subsequent to disconnection thereof from said base, and
- said flow restrictor at least partially disposed in said retained position within said open interior of said end cap, subsequent to disconnection of said flow restrictor from said base.

11. The closure assembly as recited in claim 10 further comprising a connecting structure formed on an interior surface of said housing; said connecting structure disposed and structured to define a rotational attachment and a rotational detachment of said housing onto and from the medical device.

12. The closure assembly as recited in claim 11 wherein said flow restrictor is disposed in said retained position within said housing concurrent to both said rotational attachment and said rotational detachment.

13. The closure assembly as recited in claim 11 wherein said connecting structure comprises a threaded connecting structure formed on and extending along at least a majority of a length of said interior surface between said access opening and said stop member.

14. The closure assembly as recited in claim 11 wherein said flow restrictor is disposed in said retained position within said housing, disconnected from said base, concurrent to a predetermined force applied to said flow restrictor; said predetermined force applied substantially concurrent to said rotational attachment.

15. The closure assembly as recited in claim 10 wherein said captured orientation further comprises said base movable between said stop member and said end cap.

* * * * *